United States Patent
Kobayashi

(10) Patent No.: US 10,184,938 B2
(45) Date of Patent: Jan. 22, 2019

(54) TESTING DEVICE, A TRANSFER MEMBER, A METHOD OF THE TESTING DEVICE, AND A TESTING KIT

(71) Applicant: Rie Kobayashi, Shizuoka (JP)

(72) Inventor: Rie Kobayashi, Shizuoka (JP)

(73) Assignee: Ricoh Company, Ltd., Rokyo (JP)

( * ) Notice: Subject to any disclaimer, the term of this patent is extended or adjusted under 35 U.S.C. 154(b) by 177 days.

(21) Appl. No.: 15/065,955

(22) Filed: Mar. 10, 2016

(65) Prior Publication Data
US 2016/0274100 A1    Sep. 22, 2016

(30) Foreign Application Priority Data

Mar. 19, 2015  (JP) ................................. 2015-055875

(51) Int. Cl.
*G01N 21/75*    (2006.01)
*G01N 33/558*   (2006.01)
*B01L 3/00*     (2006.01)

(52) U.S. Cl.
CPC ............ *G01N 33/558* (2013.01); *B01L 3/502* (2013.01); *B01L 2300/069* (2013.01); *B01L 2300/0825* (2013.01); *B01L 2300/161* (2013.01); *B01L 2400/0406* (2013.01)

(58) Field of Classification Search
CPC ................... G01N 33/558; B01L 3/502; B01L 2400/0406; B01L 2300/0825; B01L 2300/069; B01L 2300/161
See application file for complete search history.

(56) References Cited

U.S. PATENT DOCUMENTS 7,097,983 B2 *   8/2006  Markovsky .............. A23D 9/00
                                                      422/412

FOREIGN PATENT DOCUMENTS

| JP | 2009-85838      | 4/2009  |
|----|-----------------|---------|
| JP | 2009-250763     | 10/2009 |
| WO | WO 2015/041372  | 3/2015  |
| WO | WO 2015/041373  | 3/2015  |
| WO | WO 2015/129924  | 9/2015  |

OTHER PUBLICATIONS

U.S. Appl. No. 14/771,377, filed Aug. 28, 2015 Inventor: Kobayashi.

* cited by examiner

*Primary Examiner* — Dennis White
(74) *Attorney, Agent, or Firm* — Oblon, McClelland, Maier & Neustadt, L.L.P.

(57) ABSTRACT

A liquid sample that is supplied to a detection device can be stored at the entry portion provided in a housing of the detection device having the housing; however, there is a problem that the detection device becomes bulky due to a volume of the entry. The testing device includes a flow path member for forming a flow path of a liquid test sample, a storage member for storing the liquid test sample to be supplied to the flow path, which contacts a portion of the flow path member, and a testing material for testing the liquid test sample supplied to the flow path. The storage member expands by contacting with the liquid test sample.

19 Claims, 3 Drawing Sheets

TESTING DEVICE, A TRANSFER MEMBER, A METHOD OF THE TESTING DEVICE, AND A TESTING KIT

CROSS REFERENCE TO RELATED APPLICATIONS

This application claims priority from Japanese Application 2015-055875, filed Mar. 19, 2015, the content of which is hereby incorporated herein by reference in its entirety.

BACKGROUND OF THE INVENTION

Field of Invention

The present invention relates to a testing device, a transfer member, a method of the testing device, and a testing kit.

Discussion of the Background

A testing device for detecting an object substance included in blood, DNA, or food or drink by using a reagent has been known. The testing device has a system that includes a liquid sample including a specimen contacting with the reagent at a determination portion. A user of the testing device can determine the presence of the object substance by confirming appearance of a signal given by a reaction.

A detecting device having a detecting member composed of a porous member for chromatography is shown in Patent Literature 1 (Japanese Patent Application Laid-Open Publication No. 2009-85838). A detecting reagent which can be combined with the object substance to be detected is fixed to the detecting member in the linear state that is perpendicular to the longer direction of the detecting device. The existence of an object substance in a liquid sample can be determined by visually confirming a line which appears when the liquid sample supplied to the detecting member reaches a fixing portion of the detecting reagent.

A detecting device of Patent Literature 1 has a sample pad composed of non-woven fabric including pulp. The sample pad can store a very small quantity of a liquid sample when the liquid sample is supplied to the detecting member. Patent Literature 2 (Japanese Patent Application Laid-Open Publication No. 2009-250763) shows an immuno-chromatographic device having a housing as a device which is able to store larger quantity of a liquid sample. The housing has a pyramidal shaped entry for spreading liquid.

SUMMARY OF THE INVENTION

A liquid sample to be supplied to a detecting device can be stored at the entry portion provided for the housing in the detecting device having a housing. However, there is a problem that the detecting device becomes bulky due to the volume of the entry.

Accordingly, one object of the present invention is to provide a testing device comprising:

a flow path member for forming a flow path of a liquid test sample, a storage member for storing the liquid test sample to be supplied to the flow path, contacting a portion of the flow path member, and a testing material for testing the liquid test sample supplied to the flow path, wherein the storage member expands by contacting with the liquid test sample.

In one embodiment, the storage member could be a shape elasticity material. In another embodiment, the storage member comprises a porous synthetic resin and a water soluble resin. In yet another embodiment, the storage member forms an open-cell structural body by expansion.

In a different embodiment, porosity of the open-cell structural body could be 80% or more.

In another embodiment, an average pore diameter of the open-cell structural body is from 20 μm to 300 μm.

In another embodiment, a water soluble resin has thermoplasticity.

A different object of the present invention is to provide a transfer member comprising:

a release layer, and a storage member forming layer overlapping with the release layer and including a water storable member by expansion brought from a contact with a liquid test sample.

A different object of the present invention is to provide a manufacturing method of a testing device comprising:

transferring a storage member forming layer of a transfer member to a portion of a flow path member by compressing the storage member forming layer and the flow path member when the storage member forming layer and the flow path member face with each other.

A testing kit comprising a testing device and a sampler for sampling a liquid test sample is also provided.

The present invention reduces a size of a testing device in contrast with a testing device where an entry portion for a liquid sample is provided for the housing.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6(B) is a cross-sectional view of FIG. 6 (A) at the section of B-B.

DETAILED DESCRIPTION OF THE INVENTION

Figure 1:
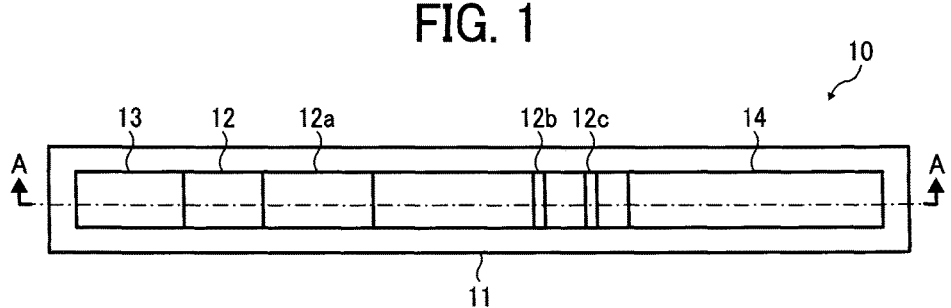
FIG. 1 is a top view of the testing device of one of the embodiments of the present invention.

All publications, patent applications, patents, and other references mentioned herein are incorporated by reference in their entirety. Further, the materials, methods, and examples are illustrative only and are not intended to be limiting, unless otherwise specified.

In the drawings, like reference numerals designate identical or corresponding parts throughout the several views. Further, as used herein, the words "a", "an" and the like generally carry a meaning of "one or more", unless stated otherwise. The drawings are generally drawn to scale unless specified otherwise or illustrating schematic structures or flowcharts. Embodiments of the present invention are explained using the figures.

<<Structures of Embodiments>>

Figure 2:
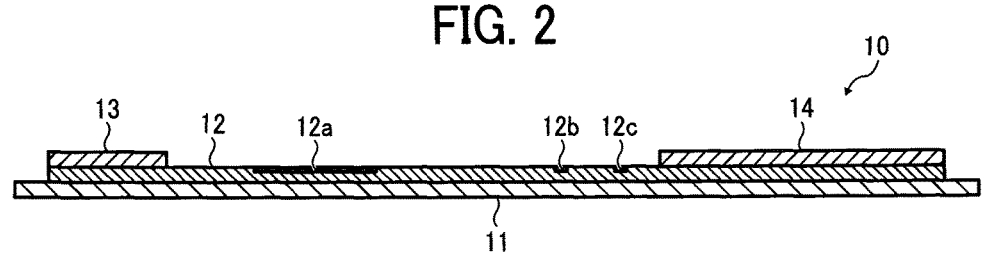
FIG. 2 is a cross-sectional view of the testing device of one of the embodiments of the present invention.
Figure 3A:
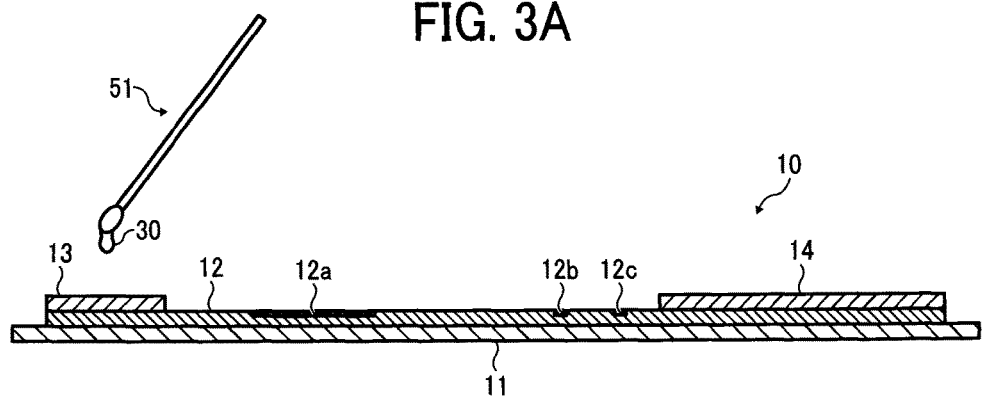
FIG. 3A, 3B are schematic diagrams of the state that is before and after dropping a liquid test sample onto a storage member.
Figure 3B:
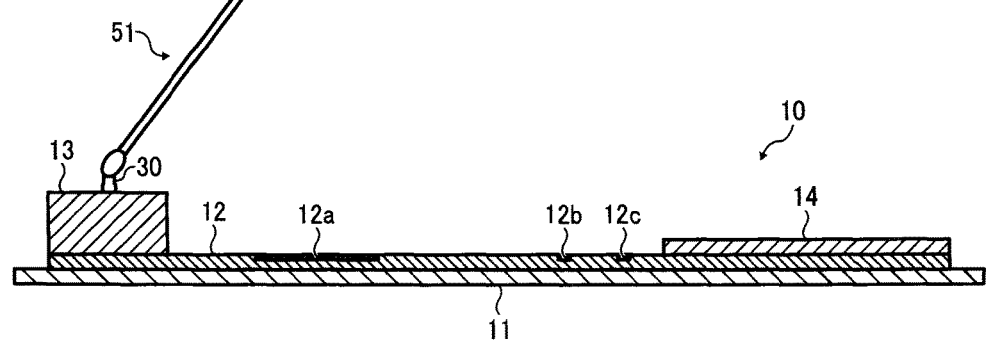

Structures of the described embodiments are explained using FIG. 1 and FIG. 2. FIG. 1 is a top view of a testing device of one of the embodiments of the present invention. FIG. 2 is a cross-sectional view of the testing device of FIG. 1 at the portion of A-A.

Testing device 10 includes substrate 11, flow path member 12, storage member 13 provided in contact with and at a part of flow path member 12, and absorbent member 14 provided in contact with and at a part of flow path member 12. In this embodiment, "provided on a member" means "provided in contact with the member"

Specific examples of a liquid test sample which could be analyzed include a hydrophilic sample such as blood, cerebrospinal fluid, urine, and a liquid test sample including a specimen collected with a collecting means, e.g. a stick and similar tools.

In this embodiment, a testing device, including a device for detecting an antigen that is contained in a liquid test sample, is shown, but the types of a testing device are not limited to the device using an antigen-antibody reaction. For example, a testing device that detects a particular component by using a reagent which changes in hue accompanying with its structural change is available.

<<<About Each Member>>>
<<Substrate>>

In one embodiment, substrate 11 is, but is not limited to, an organic substrate, an inorganic substrate, a metallic substrate or a similar substrate, and can be selected according to an objective. It is preferred that at least one surface of substrate 11 is covered with a hydrophobic resin, but the present invention is not limited to this embodiment. When a testing device is used as a sensor chip, preferably a synthetic resin is used as substrate 11 in terms of lighter weight, flexibility, and low price. In one embodiment, a high durable substrate such as a plastic sheet can be used, consequently the durability of testing device 10 can be improved.

Specific examples of substrate 11 include, but are not limited to, a substrate made of at least one of polyvinyl chloride, polyethylene terephthalate, polypropylene, polyvinyl acetate, polycarbonate, polyacetal, modified-polyphenylether, polybutylenephthalate, and ABS resin. Preferably the substrate is a substrate made of polyethylene terephthalate in terms of low cost and availability.

A form of substrate 11 is not limited, but a sheet type is preferred. An average thickness of substrate 11 is not limited and is selected in accordance with an object of the present invention, and is preferably from 0.01 mm to 0.5 mm. When the average thickness is less than 0.01 mm, substrate 11 may be insufficient in strength. When the average thickness is more than 0.5 mm, substrate 11 may be insufficient in flexibility depending on the materials, and it may be difficult to handle it as a sensor. The average thickness is defined as an average value of thickness measured for 15 measurement points which are arranged in 5 columns and 3 rows at almost uniform intervals with a micrometer. "Thickness" can be defined as a length which is perpendicular to the contact surface between the substrate and flow path member 12.

<<Storage Member>>

In testing device 10, storage member 13 is in contact with a part of flow path member 12 and is provided at the portion where a liquid test sample is dropped. At first, storage member 13 temporarily stores the liquid test sample which is going to flow to a flow path of flow path member 12, and then the stored liquid test sample gradually flows to flow path member 12. A shape elastic material which expands (and can be restored to the original shape) by shape elasticity when is in contact with the liquid test sample, is used for a component of storage member 13. In one embodiment, a compressed sponge (a porous synthetic resin having elasticity) is used as the shape elastic material.

A sponge is made of a hydrophilic material having a water-insoluble property or poor water-soluble property. Specific examples of the hydrophilic material include, but are not limited to, a PVA (polyvinyl alcohol) resin and a hydrophilized resin such as a hydrophillic polyurethane resin and a hydrophillic PVC (polyvinyl chloride) resin. Among the hydrophilic materials, PVA is preferred in terms of water retention property. "Water-insoluble property" means that materials are substantially insoluble in water. "Substantially insoluble in water" means that a difference in mass quantity between a resin product immersed in large quantity of water at 25° C. or less for 24 hours and a resin product sufficiently dried by a vacuum drying method after the immersion is 1 mass % or less in consideration of mass decrease caused by dissolution of by-products (e.g. monomer) included in the resin.

"Poorly water-soluble property" means that a difference in mass quantity between a resin product immersed in large quantity of water at 25° C. or less for 24 hours and a resin product sufficiently dried by a vacuum drying method after the immersion is 10 mass % or less. In one embodiment, a sponge is dried by evaporation of water prior to dissolution of a resin product in water with the lapse of time and, therefore, both a hydrophilic material having a water-insoluble property and a hydrophilic material having a poor a water-soluble property can be used.

A mechanically compressed sponge can be used as storage member 13; however, it may be restored to the original shape little by little with the lapse of time. Therefore, it is preferable to keep the form of a sponge by compressing with providing voids with a small quantity of a fixing material. A water soluble resin is preferably used as a fixing material. Specific examples of the water soluble resin include PVP (polyvinylpyrrolidone), PVA (polyvinyl alcohol), PEG (polyethylene glycol), and PEO (polyethylene oxide). A resin such as PVA can be used as the fixing material or a component of a sponge by modifying degree of polymerization or a substituent.

A sponge keeping the compressed form with a water soluble resin can be obtained by thinly coating surfaces and inside of the sponge with a water soluble resin by immersing the sponge in a water soluble resin dissolved solution, compressing the coated sponge, and then drying the compressed sponge so that the compressed form is kept.

Preferably, the content of the water soluble resin to the total mass of storage member 13 (including a water soluble resin) is from 0.05 mass % to 0.6 mass %. When the content of the water soluble resin is 0.6 mass % or more, the compressed sponge may not expand by contacting with a liquid test sample and may not be restored to its original form. When the content of the water soluble resin is 0.05 mass % or less, the compressed sponge may lose adhesiveness to keep the compressed form.

It is preferred to use a water soluble resin having thermoplasticity so as to provide storage member 13 on flow path member 12 by thermal transfer. When the water soluble resin having thermoplasticity is used, the water soluble resin is melted by heat and followed by elution of some of the water soluble resin from transfer material, and then the storage member is adhered onto flow path member 12. Specific examples of the water soluble resin having thermoplasticity include PVP, PEG, and PEO, wherein PVP is preferred in terms of easiness of thermal transfer (low viscosity in thermofusion).

An open-cell structural body is formed by expanding the compressed sponge. The open-cell structural body is one of porous materials, has pores continuously connected with each other, and is different from a closed-cell structural body that does not have pores continuously connected with each other. The open-cell structural body has opening on the walls of cells, and can take liquid and pass air.

In one embodiment, porosity (%) of the sponge (open-cell structural body) means a volume fraction of pores formed in the sponge in the original or restored state to the apparent volume of the sponge in the original or restored state. Preferable, porosity of the sponge is 80% or more. When porosity of the sponge is less than 80%, quantity of stored liquid may be insufficient and the restored sponge may not be able to store a liquid test sample in the needed amount.

A preferred average pore diameter of the sponge in the original or restored state (open-cell structural body) is from 20 μm to 300 μm. When the average pore diameter is less than 20 μm, a water holding property of the sponge may become too high, and the liquid test sample filled in the sponge may not be supplied to flow path member 12. When an average pore diameter is more than 300 μm, a water releasing property of the sponge may become too high, and the liquid test sample filled in the sponge may not be held and may leak from the side that is not in contact with flow path member 12. An average pore diameter of the sponge is defined as an average value of a major axes (a length of the long diameter) of the predetermined number of pores selected from plural pores that exist in the sponge in accordance with the predetermined standard. An average pore diameter can be measured by the following measurement:

cutting a sponge at the predetermined portion, and taking a photo of the internal texture exposed at the cutting surface with an electron microscope;

selecting top 20 pores with the longest major axis from the plural pores existing in the predetermined area of the taken photo;

measuring the major axis of each of selected 20 pores;

then calculating the average of the measured major axes of 11th to 20th largest pores of the 20 pores, thereby the average pore diameter can be obtained.

A liquid test sample is transferred from storage member 13 to flow path member 12 by the capillary phenomenon. Rising height Z of liquid (a liquid surface) by the capillary phenomenon is calculated by the following formula:

$$Z=2T \cos \theta / \rho gr;$$

wherein T=surface tension, θ=contact angle, ρ=density of liquid, g=gravity acceleration, r=inside diameter of tube (radius).

It is considered that the smaller the inside diameter of a tube (i.e., a pore diameter of the porous material) is, the higher absorption force of the capillary, when both storage member 13 and flow path member 12 are made of a hydrophilic porous material, and when the same liquid sample flows through both storage member 13 and flow path member 12. Therefore, it is preferred that a pore diameter of flow path member 12 is smaller than that of storage member 13. Thus, a liquid sample stored at storage member 13 can be easily transferred to flow path member 12 by having higher absorption force by the capillary phenomenon in flow path member 12. By having absorption force by the capillary phenomenon in absorbent member 14 much higher, the backflow becomes difficult to occur and almost the entire liquid test sample can transfer from storage member 13 to flow path member 12.

A schematic diagram of the state that is after dropping liquid test sample 30 onto storage member 13 is described hereinafter. A water soluble resin for holding compressing state of a sponge dissolves to the liquid test sample in storage member 13 when the hydrophilic liquid test sample taken with sterile cotton swab 51 (a sampler) is added to storage member 13. Then the sponge restores its original shape because it becomes difficult to hold the compression state due to dissolution of a water soluble resin. The sponge expands in the opposite direction of the compressing direction, preferably it expands in the thickness direction crossing at a right angle with the counter surface to the flow path member.

In testing device 10, a predetermined quantity of a liquid test sample can be stored at the sponge without a housing having an opening for entry of the liquid test sample. Testing device 10 can be miniaturized by compression of a sponge. Further, the sponge stores a liquid test sample by the capillary phenomenon, therefore leakage of the liquid test sample is more difficult than when a liquid test sample is stored at the entry of the housing.

In one embodiment, a preferable expansion coefficient of storage member is 3 or more. When the expansion coefficient is less than 3, it may be difficult to take advantage of the reducing size of storage member 13 because of insufficient compression of the sponge. Further, the quantity of a storable liquid test sample may be small because of the small volume of restored storage member 13 even though the sponge is compressed. The upper limit of the expansion coefficient or the maximum compression ratio is physically determined by the porosity of the sponge. If compression is over the maximum compression ratio of storage member 13, the storage member may be separated from testing device 10 during the expansion, because the sponge has stretched in the lateral direction.

The expansion coefficient of storage member 13 is a ratio of the thickness change of storage member 13 caused by the expansion. The expansion coefficient of storage member 13 can be measured as follows. A thickness change caused by the expansion is measured at 5 points which includes four corners of a rectangle measurement sample of storage member 13 and the intersection point of diagonal lines, and the average value of top 3 points with the highest expansion coefficient is calculated as the expansion coefficient of storage member 13.

A preferred thickness of storage member 13 is, but is not limited to, from 30 μm to 1000 μm. When the thickness of storage member 13 is more than 1000 μm, testing device 10 may be bulky. When the thickness of storage member 13 is less than 30 μm, quantity of a storable liquid test sample may be insufficient. The preferred range depends on thickness and length, therefore a different range may be selected.

<<A Flow Path Member>>

Examples of flow path member 12 of testing device 10 include, but are not limited to, as long as it is able to flow liquid test sample 30, a hydrophilic porous material. The flow path member formed of the hydrophilic porous material has pores, and liquid test sample 30 flows through the pores. It is preferred that the hydrophilic porous material has an open-cell structural body where pores are connected with each other. An open-cell structure is different from a closed-cell structure where pores exist independently. The open-cell structural body has opening on the walls of cells, and can take liquid by the capillary phenomenon and pass air. The flow path member can transfer liquid test sample 30 by the capillary phenomenon at the pores without external driving equipment such as a pump.

Examples of the hydrophilic porous material include, but are not limited to, a substrate having hydrophilicity and high porosity, wherein the hydrophilic porous material can be selected according to an objective. The hydrophilic porous material is a porous material having high water permeation. The high water permeation is a property when 0.01 mL of water entirely penetrate in 10 minutes in the evaluation test for water penetration where 0.01 mL of water is dropped on the surface of a plate test piece which is thereafter dried for 1 hour at 120° C.

The preferred porosity of the hydrophilic porous material is, but is not limited to, from 40% to 90%, wherein the hydrophilic porous material can be selected according to an objective. More preferably, the porosity is from 65% to 80%. When the porosity is more than 90%, strength of the substrate may not be maintained. When the porosity is less than 40%, permeation of a liquid test sample 30 may become low. The porosity is calculated from the following formula 1 using paper weight in grams per square meter of the hydrophilic porous material (g/m$^2$), thickness of the hydrophilic porous material (μm), and component specific gravity of the hydrophilic porous material:

Porosity (%)={1−[Paper weight in grams per square meter (g/m$^2$)/Thickness (μm)/Component specific gravity]}×100.  [Formula 1]

Specific examples of the hydrophilic porous material include, but is not limited to, a filter paper, a plain paper, a pure paper, a watercolor paper, a kent paper, a synthetic paper, a synthetic resin film, a specific paper having a coat layer, a fabric, a fiber product, a film, an inorganic substrate, and a glass, wherein the hydrophilicity porous material could be selected in accordance with an object of the present invention.

Specific examples of fabric include man-made fibers such as rayon, bemberg, acetate, nylon, polyester, and vinylon; natural fibers such as cotton and silk; mixed fibers, and nonwoven fabric.

Among the hydrophilic porous material, filter paper is preferable in terms of high porosity and high hydrophilicity. When the testing device is used for a biosensor, fiber paper is suitable for a stationary phase of paper chromatography. A filter paper used for a known testing device (e.g. nitrocellulose membrane filter) is suitably used.

A preferred form of the hydrophilic porous material is, but is not limited to, a sheet type, and can be selected in accordance with an objective. An average thickness of the hydrophilic porous material is, but is not limited to, from 0.01 mm to 0.3 mm, and can be selected in accordance with an objective. When the average thickness is less than 0.01 mm, strength of the hydrophilicity porous material as a substrate may be insufficient. When the average thickness is more than 0.3 mm, the amount of the hydrophilic porous material needed for liquid test sample 30 may be too high.

A reagent is applied on portions of flow path member 12, and thus conjugation part 12a, test line 12b, and control line 12c are provided on flow path member 12.

A marker antibody that reacts with an object antigen to be detected is applied as a reagent on conjugation part 12a. Examples of the marker antibody include colloidal gold anti-human IgG. The marker antibody flows out from the hydrophilic porous material when the liquid test sample comes through flow path member 12 and reaches conjugation part 12a. When the liquid test sample includes the object antigen, the object antigen reacts with the marker antibody by an antigen-antibody reaction, and thereby an antigen-marker antibody complex is produced.

A detection antibody that reacts with the object antigen to be detected is applied as a reagent on test line 12a. A detection antibody such anti-human IgG can be used. When the antigen-marker antibody complex is produced, the antigen-marker antibody complex is captured by a capturing antibody which is fixed to test line 12b, and thereby test line 12b shows a color.

A controlling antibody such as human IgG is applied and fixed to control line 12c. The controlling antibody is not limited as long as it can capture a marker antigen that flows out from conjugation part 12a. When the marker antigen that flows out from conjugation part 12a reaches control line 12c, it is captured by the controlling antibody fixed to control line 12c and thereby control line 12c shows a color. A user of the testing device can confirm that the liquid test sample reaches control line 12c.

The above mentioned reagents are examples of a testing material for testing a liquid test sample that flows into flow path member 12. Examples of the testing material further include a testing material where each of the above mentioned reagents can be fixed to at least one surface of a resin layer. In this case, a testing device is made by attaching to the surface, where any of the above mentioned reagents can be fixed, to any of flow path member 12, conjugation part 12a, test line 12b, and control line 12c.

<<Absorption Member>>

Examples of absorbent member 14 are not limited as long as the member has water absorption, and can be selected from the known materials. Specific examples of absorbent member 14 include a paper, a fabric, a polymer compound having a carboxyl group or salt thereof, a partially crosslinked material having a carboxyl group or salt thereof, and a partially crosslinked material of polysaccharide.

<<<Transfer Member>>>

In one embodiment, storage member 13 can be provided on flow path member 12 by transferring the storage member forming layer for forming storage member 13 onto a portion of flow path member 12. A preferred transfer member for the transfer is a transfer member having a three-layer structure of a support, a release layer formed over the support, and the storage member forming layer formed over the release layer.

Figure 4:
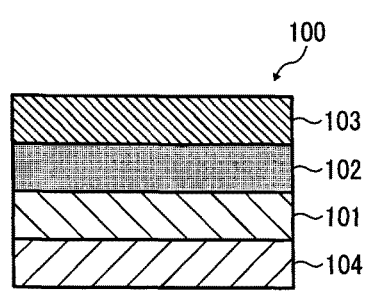
FIG. 4 is a cross-sectional view of a transfer member of one of the embodiments of the present invention.

The transfer member is explained based on FIG. 4. FIG. 4 shows a cross sectional view of the transfer member of one embodiment of the present invention. Transfer member 100 includes support 101, release layer 102 formed over support 101, and a storage member forming layer formed over release layer 102. The transfer member may further include back layer 104 which could be formed as needed.

—Support—

A form of the substrate, structure of the substrate, size of the substrate, and a material of the substrate are not limited and could be selected in accordance with an objective. As for the structure, either a mono-layer structure or a multi-layer structure can be available. A size of the substrate is selected in accordance with the size of testing device 10.

Specific examples of the material of support 101 include, but are not limited to, polyester (e.g. polyethylene terephthalate (PET) and polyethylene naphthalate (PEN)), polycarbonate, polyimide (PI), polyamide, polyethylene, polypropylene, polyvinyl chloride, polystyrene, styrene-acrylonitrille copolymer, and cellulose acetate, and could be selected in accordance with an objective. These materials can be used independently or in combination. Among these materials, polyethylene terephthalate (PET) and polyethylene naphthalate (PEN) are preferred.

It is preferable to apply surface-active treatment to a surface of substrate 101 to improve adhesiveness between the surface of substrate 101 and a layer to be formed thereon.

Support 101 can either remain over testing device 10 or be removed from testing device 10 after transfer. Support 101 is not limited and could be suitably made or could be a commercially available support. A preferable thickness of the support is, but is not limited to, from 3 µm or more to 50 µm or less, and can be selected according to an objective.

—Release Layer—

Release layer 102 can assist support 101 and storage member forming layer 103 in releasing thereof in transfer. Release layer 102 becomes liquid having a low viscosity by heating with a heating pressurizing apparatus such as a thermal head, and, thereby, storage member forming layer 103 can be easily released near the interface of a heated potion and unheated portion. Release layer 102 includes wax and a binder resin, and further includes other components as necessary.

Specific examples of waxes include, but are not limited to, natural wax (e.g. bees wax, carnauba wax, spermaceti, Japan tallow, candelilla wax, rice bran wax, and montan wax), synthetic wax (e.g. paraffin, microcrystalline wax, oxidized wax, ozokerite, ceresine, ester wax, and polyethylene wax), higher fatty acid (e.g. oxidized polyethylene wax, synthetic wax, margaric acid, lauric acid, myristic acid, palmitic acid, stearic acid, furoic acid, and behenic acid), higher alcohol (e.g. stearyl alcohol and behenyl alcohol), ester (e.g. corbitan-fatty acid ester), and amide (e.g. octadecanamide and oleic amide), and can selected in accordance with an objective. These waxes can be used independently or in combination. Among the above-mentioned waxes, carnauba wax and polyethylene wax are preferred in terms of the high releasing property.

Specific examples of a binder resin include, but are not limited to, ethylene-vinyl acetate copolymer, partially saponified ethylene-vinyl acetate copolymer, ethylene vinyl-alcohol copolymer, ethylene-methacrylate sodium copolymers, polyamide, polyester, polyurethane, polyvinyl alcohol, methyl cellulose, carboxymethyl cellulose, starch, polyacrylic acid, isobutylene-maleic acid copolymer, styrene-maleic acid copolymer, polyacrylamide, polyvinyl acetal, polyvinyl chloride, polyvinylidene chloride, isoprene rubber, styrene-butadiene rubber copolymer, ethylene propylene copolymer, butyl rubber, and acrylonitrile-butadiene copolymer, and can be selected according to an objective. The binder resins can be used independently or in combination.

Examples of the forming method of release layer 102 include, but are not limited to, a hot melt coating method, and a method of applying application liquid where wax and/or a binder resin is/are included in a solvent, and can be selected according to an objective. A preferred average thickness of release layer 102 is, but not is limited to, from 0.5 µm to 50 µm, and can be selected according to an objective. The coating quantity of release layer 102 is, but not limited to, from 0.5 g/m² to 50 g/m², and can be selected according to an objective —A Storage Member Forming Layer—

Storage member forming layer 103 provides a storage portion in testing device 10 when storage member forming layer 103 is transferred to the flow path member. Storage member forming layer 103 includes a material which expands by contact with a liquid test sample and is able to store the liquid test sample. Specifically, storage member forming layer 103 includes a sponge composed of storage member 13 and a material such as a water soluble resin having thermoplasticity. Examples of the method of forming storage member forming layer 103 include, but are not limited to, a method where sponges each including a water soluble layered are laminated over release layer 102 and compressed with a press machine, and can be selected according to an objective. The sponges are compressed, thereby the sponges are expanded by contact with a liquid test sample and the liquid test sample can be stored. Examples of the compressing condition include, but are not limited to, a condition where a compression pressure is from 10 MPa to 30 MPa, and a compression time is from 1 minute to 16 hours, and can be selected according to an objective. The preferable range depends on quality and thickness of a sheet, and can be selected from other conditions mentioned above.

—A Back Layer—

It is preferred that back layer 104 is provided with transfer member 100 so that back layer 104 is over the surface on the opposite side of support 101 from the surface facing release layer 102. The surface on the opposite side from the surface facing release layer 102 is directly heated with a thermal head in a transfer process. It is preferred that back layer 104 has a high heat resistance and rub resistance to the thermal head. Back layer 104 includes a binder resin and further includes other components as necessary.

Specific examples of the binder resin include, but are not limited to, a silicone-modified urethane resin, silicone-modified acrylic resin, silicone resin, silicone rubber, fluororesin, polyimide resin, epoxy resin, phenol resin, melamine resin, and nitrocellulose, and can be selected according to an objective. The binder resins can be used independently or in combination.

Specific examples of other component include, but are not limited to, fine particles of talc, silica, organopolysiloxane, and lubricant, and can be selected according to an objective.

Examples of a method of manufacturing back layer 104 include, but are not limited to, general application methods such as a gravure coater method, a wire bar coater method, and a roll coater method, and can be selected according to an objective. A preferred average thickness of back layer 104 is, but is not limited to, from 0.01 µm or more to 1.0 µm or less, and can be selected according to an objective.

<<Transferring of the Storage Member Forming Layer>>

Examples of a method for heat transferring storage member forming layer 103 onto flow path member 12 include a method where storage member forming layer 103 over transfer member 100 and flow path member 12 face each other and are pressed and heated so that storage member forming layer 103 is transferred onto a part of flow path member 12. Examples of a printer for the heat transferring include, but are not limited to, a thermal printer having a serial type thermal head or a line type thermal head. Preferable applied energy of the heat transferring is, but is not limited to, from 0.05 mJ/dot to 0.5 mJ/dot, and can be selected according to an objective. When the applied energy is less than 0.05 mJ/dot, a water soluble resin having thermoplasticity may not be sufficiently melted. When the applied energy is more than 0.5 mJ/dot, a reagent may be denatured by heat, or other parts of transfer member 100, and then the water soluble resin may be melted and may adhered to a thermal head.

<<A Use of the Testing Device>>

Specific examples of use of testing device 10 include, but are not limited to, a biochemical sensor (sensing chip) for a blood test or a DNA test, and a small sized analytical instrument (chemical sensor) for quality control of food or drinks, and can be selected according to an objective.

Examples of a test sample (specimen) for a biochemical test include, but are not limited to, a pathogen (e.g. a bacteria and a virus), a sample taken from a living body (e.g. blood, saliva, and a histological disease test piece), and excreta (e.g. an excrement and urine), and can be selected according to an objective. Further, an example of the test sample is a sample for prenatal diagnosis (e.g. fetal cells included in amniotic fluid and invitro divided oocyte). The test samples can be pretreated with cell-disruption treatment such as enzymatic treatment, heat treatment, surfactant treatment, ultrasonic treatment, and a combination of the treatments directly or after being concentrated as hypostasis by centrifugation if necessary.

Testing device 10 of one embodiment can chromatograph (separate or purify) a liquid test sample because flow path member 12 works as a stationary phase. In that case, flow path member 12 having hydrophilicity inside of the open-cell structure works as the stationary phase (carrier). The flow velocity of each component of the liquid test sample flowing through the flow path is different because the flow velocity of each component depends on the strength of their interaction with the stationary phase (the velocity of each component depends on the grade of hydrophilicity/hydrophobicity of each component).

A component having high hydrophilicity is easily adsorbed by pores of the stationary phase and repeats adsorption to the pores and desorption from the pores more frequently, and, therefore, the flow velocity of the component having high hydrophilicity is low. Yet, a component having high hydrophobicity flows without adsorption to the pores, and, therefore, the flow velocity of the component having high hydrophobicity is high. Testing device 10 can be used as a high functional chemical sensor or a high functional biochemical sensor when a subject component is separated from other components included in a liquid test sample and is reacted with a reagent by using a difference in the flow velocity of the components included in the liquid test sample.

<<A Testing Method>>

A testing method using testing device 10 can include, but is not limited to, the following process:
(1) Dropping liquid test sample 30 to storage member 13,
(2) Transferring liquid test sample 30 from storage member 13 to the flow path member by the capillary phenomenon,
(3) Releasing a marker antigen from conjugation part 12a by contacting the marker antigen with liquid test sample 30,
(4) Producing an antigen-marker antibody complex by an antigen-marker antibody reaction when the object antigen is included in liquid test sample 30,
(5) Capturing the antigen-marker antibody complex at test line 12b by contact between an antibody fixed to test line 12b and a liquid test sample including the antigen-marker antibody complex.
(6) Capturing the marker antibody complex at control line 12c by contact between an antibody fixed to control line 12c and a liquid test sample including the marker antibody.

<<A Testing Kit>>

Figure 5:
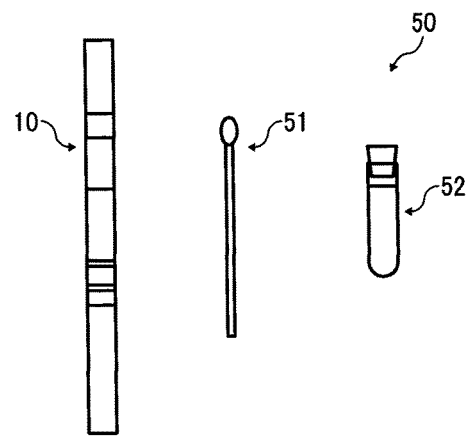
FIG. 5 is a schematic diagram of a testing kit of one of the embodiments of the present invention.

Testing kit 50 including testing device 10, a sampler for collecting a specimen or a liquid test sample (an example of a sampler), and liquid for treating the specimen as shown in FIG. 5 can be used for inspection conducted by the above mentioned testing method. FIG. 5 is a schematic diagram of a testing kit relating to one embodiment of the present invention. Examples of the sampler for collecting a specimen or a liquid test sample include a known sampler such as a sterile cotton swab 51 for collecting a specimen from the pharynx or the nasal cavity. Examples of liquid for treating the specimen include known liquid such as dilution liquid 52 for diluting a specimen to use the dilution liquid as the liquid test sample, and an extraction liquid for extracting the specimen to use the extraction liquid as the liquid test sample.

<<Supplementation for the Embodiment>>

In the above mentioned embodiment, the reagent is an antigen or an antibody; however the present invention is not limited to this embodiment. An indicator used for the chemical assay is a reagent which indicates a chemical property of liquid. Examples of the indicator include, but are not limited to, various types of ionophores that change color by reacting with various types of ions such as a pH indicator, lead ion, cupper ion, and nitrite ion, and a reagent which change colors by reacting with various types of agricultural chemicals.

A transferring process where storage member forming layer 103 is released from transfer member 100 by heating is given as an example in the above embodiment. The release of storage member forming layer 103 can be carried out by using light. Storage member forming layer 103 can be released by melting of release layer 102 including a light absorption agent (e.g. carbon black), where heat for melting is generated by having release layer 102 absorb light. Also, storage member forming layer 103 can be released by deterioration of release layer 102 including the material which changes its quality by irradiation of light, where heat for the deterioration is caused by having release layer 102 absorb light.

The above mentioned embodiment is an example where the flow path is formed on the entire flow path member 12, but the present invention is not limited to this example. Examples of the method of forming a flow path on a part of flow path member 12 include a method of forming a flow path wall, which becomes outline of the flow path, by having a hydrophobic material filled with pores of a hydrophilicity porous member by a known method.

A protective member can be provided for testing device 10 to avoid contamination from hands when flow path member 12 is handled. Examples of the protective member include a housing completely covering testing device 10 and a film provided over flow path member 12. In case of providing the protective portion, it is preferred that an opening for dropping a liquid test sample is provided at the overlapping portion with storage member 13. Further, it is preferred that an opening for releasing pressure inside the flow path is provided. It is possible to have testing device 10 less bulky, because the entry for storing a liquid test sample is not necessary to be provided for the protective member or the housing even if the protective member or the housing is provided.

Liquid test sample 30 is hydrophilic in the above mentioned embodiment, but the present invention is not limited to this example. Examples of the liquid test sample include liquid having affinity for a specific solvent and include an organic solvent (e.g., alcohols such as methyl alcohol, ethyl alcohol, 1-propyl alcohol, and 2-propyl alcohol, ketons such as acetone, MEK (methyl ethyl ketone)). "Hydrophilic" in the above mentioned embodiment is substituted with "hydrophobic", and "hydrophobic" in the above mentioned embodiment is substituted with "hydrophilic".

All ranges described in this application include all values and subvalues therebetween.

Having generally described this invention, a further understanding can be obtained by reference to certain specific examples which are provided herein for purposes of illustration only, and are not intended to be limiting unless otherwise specified.

EXAMPLES

The porosity of a sponge before being compressed and an average pore diameter of the sponge used in the Examples and Comparative Examples are shown in Table 1. The porosity of a sponge is measured in accordance with a measurement method of porosity of a hydrophilic porous material, which is mentioned in the above embodiments. The average pore diameter was measured in accordance with a measurement method which is mentioned in the above embodiments.

Example 1

Figure 6A:
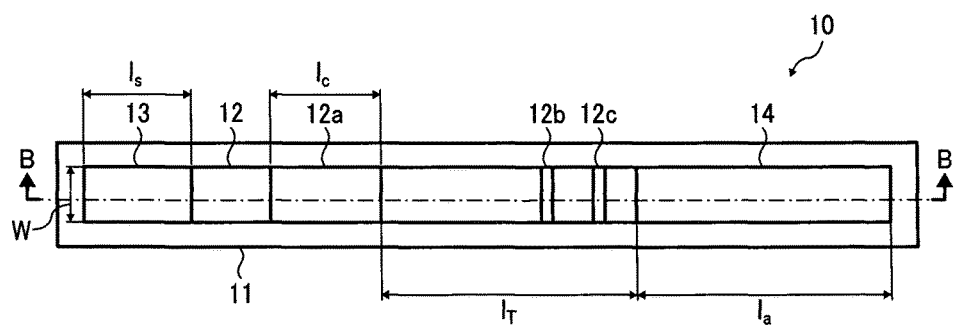
FIG. 6A, 6B is a testing device of an example.
Figure 6B:
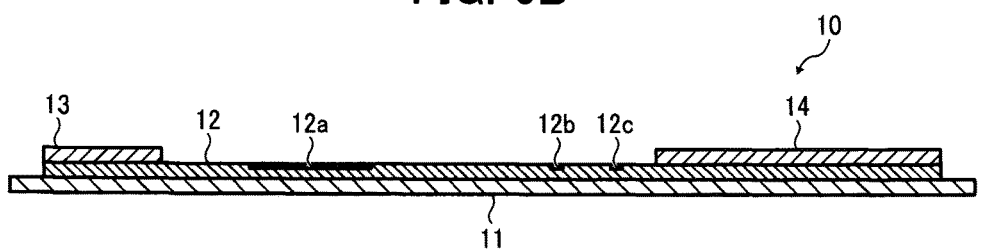

The top of a testing device of Example 1 is shown in FIG. 6(A). FIG. 6(B) is a cross-sectional view of FIG. 6 (A) at the section of B-B. In FIG. 6 (A), $I_s$ is 32 mm, $I_c$ is 15 mm, $I_T$ is 18 mm, $I_a$ is 25 mm, and w is 3.5 mm.

<<Preparing for a Member for Liquid Flow>>

Substrate 11 and flow path member 12 were adhered by the following method, and a member for liquid flow (a hydrophilic porous substrate having a hydrophobic substrate) was formed.

<<Manufacturing of a Hydrophilic Porous Substrate having a Hydrophobic Substrate>>

An adhesive layer was formed on substrate 11, which was cut out of a PET film (manufactured by Toray Industries, Inc., Lumirror S10, 50 μm) so as to have a width of 7.5 mm and length of 95 mm, by applying a polyester hot melt adhesive (manufactured by TOAGOSEI CO., LTD., ARON MELT PES 375S40) heated to 190° C. with a roll coater so that the thickness of the adhesive layer becomes 50 μm. After the adhesive layer with the applied substrate was settled for 2 hours or more, flow path member 12, which was cut from a nitrocellulose membrane filter (HF180, manufactured by Merck Millipore, thickness: 135 μm, porosity: 70%) so as to have a width of 3.5 mm and length of 95 mm, was laid over the adhesive layer and weight of 1 kgf/cm² was added at 150° C. for 10 seconds, thereby a hydrophilic porous substrate having a hydrophobic substrate was obtained.

<<Formation of a Testing Portion>>
<Formation of a Test Line and a Control Line>

6 μL of an anti-human IgG antibody (4.7 mg/mL, I1886, manufactured by Sigma-Aldrich Corporation) was applied on the hydrophilic porous substrate (flow path member 12) so that test line 12b having a width of 1 mm was formed. In a similar manner, 6 μL of human IgG (4.8 mg/mL, I2511-10MG, manufactured by Sigma-Aldrich Corporation) was applied on the hydrophilic porous substrate so that control line 12c having a width of 1 mm was formed. After this process, the hydrophilic porous substrate was dried at room temperature for 16 hours.

<Application of a Marker Antibody>

5 μL of colloidal gold anti-human IgG (Gold 40 nm, OD=15, manufactured by BAW) was applied over the hydrophilic porous substrate as a colloidal gold marker antibody so that conjugation part 12a was formed.

<<Formation of a Storage Portion>>
<Preparation for a Storage Material>

A PVA sponge having a thickness of 1000 μm (Bell-eater D, manufactured by Fuji Chemical Industries, Ltd.) was sufficiently dipped in 0.5 mass % of a polyvinylpyrrolidone aqueous solution (Polyvinylpyrrolidone K15, manufactured by Tokyo Chemical Industry Co., Ltd.), excessive liquid was lightly removed from the dipped PVA sponge, and then the PVA sponge was compressed with a press machine (High Pressure Jack J-1, manufactured by Hayashi Kougyou Kabushikikaisha) at 28 MPa for 5 hours. The compressed PVA sponge was dried with a vacuum dryer at room temperature for 1 hour, thereby a storage material having thickness of 169 μm was obtained.

<Formation of a Storage Portion>

The above formed storage material was cut into a piece having a rectangle shape having a width of 3.5 mm and a length of 32 mm, and was adhered onto the hydrophilic porous substrate, thereby storage member 13 was provided for the hydrophilic porous substrate.

<<Formation of an Absorbent Portion>>

Absorbent member 14, which was cut from an absorbent pad (CFSP223000, manufactured by Merck Millipore) so as to have a width of 3.5 mm and a length of 25 mm, was adhered onto the hydrophilic porous substrate.

As mentioned above, testing device 10 for an immunochromatographic assay was obtained.

Then the following evaluation was conducted, results of which are shown in Table 2.

(Evaluation of Leakage)

100 μL of PBS (phosphate buffered saline: D86620, manufactured by Sigma-Aldrich Corporation) as a liquid test sample for evaluation was dropped on the storage portion, and then the testing device was tilted up to 30 degrees, where it was determined whether the liquid test sample leaked from the testing device. The symbol "O" means that the leakage of the liquid test sample was not observed and the symbol "X" means that the leakage of the liquid test sample was observed. As for Comparative example 1, a storage portion of the housing case had a cup-shape, therefore the liquid test sample was leaking by tilting and the evaluation could not be conducted. Results of the evaluation are shown in the Table 2.

(Evaluation of Stability of Compressional State)

The thickness (μm) of storage member 13 was measured 2 months after its manufacture, and it was determined whether the compressed state was maintained.

Stability [times]=thickness at 2 months after its manufacture B/thickness just after its manufacture A.

(Evaluation of Restorability)

0.1 mL of water was dropped on storage member 13 which was cut into a piece of a rectangle shape having a width of 45 mm and a length of 3.5 mm, wherein the thickness of storage member 13 was measured 5 seconds after the dropping, and was evaluated how much the thickness of storage member 13 had been restored with respect to its original thickness (i.e. the thickness of the storage member before being compressed).

Restorability [%]=thickness of the restored storage member B/thickness of the original storage member A×100.

(Evaluation of Water Releasing Property)

The evaluation of the water releasing property was conducted by measuring the amount of released liquid.

A sample, which was prepared by storing 0.4 mL (0.4 g) of water in the storage member which was cut into a piece having a square shape having a width of 20 mm and a length of 20 mm, was settled over a membrane (HF180, manufactured by Merck Millipore) for 30 seconds, the amount of water which had released from the sample and soaked into the membrane during this period was measured, and then the water releasing property was evaluated using the following formula.

Water releasing property [%]=quantity of water which transferred to the membrane [g]/0.4 [g]× 100.

Example 2

A testing device of Example 2 was manufactured in a similar manner to that of Example 1 except for that polyethylene oxide (ALKOX L-6, manufactured by Meisei Chemical Works, Ltd.) was used instead of polyvinylpyrrolidone, and stability of the compressional state, restorability, water releasing property, and leakage were evaluated. Results of the evaluation are shown in the Table 2.

Example 3

A testing device of Example 3 was manufactured in a similar manner to that of Example 1 except for that PVA (Gohsenx Z, manufactured by Nippon Synthetic Chemical Industry Co., Ltd.) was used instead of polyvinylpyrrolidone, and stability of the compressional state, restorability, water releasing property, and leakage were evaluated. Results of the evaluation are shown in the Table 2.

Example 4

A testing device of Example 4 was manufactured in a similar manner to that of Example 1 except for that a urethane sponge (Sofras N tyape, manufactured by Fuji Chemical Industries, Ltd.) was used instead of the PVA sponge, and stability of the compressional state, restorability, water releasing property, and leakage were evaluated. Results of the evaluation are shown in the Table 2.

Example 5

A testing device of Example 5 was manufactured in a similar manner to that of Example 1 except for that 0.1 mass % rather than 0.5 mass % of a polyvinylpyrrolidone aqueous solution was used, and stability of the compressional state, restorability, water releasing property, and leakage were evaluated. Results of the evaluation are shown in the Table 2.

Example 6

A testing device of Example 6 was manufactured in a similar manner to that of Example 1 except for that 0.8 mass % rather than 0.5 mass % of a polyvinylpyrrolidone aqueous solution was used, and stability of the compressional state, restorability, water releasing property, and leakage were evaluated. Results of the evaluation are shown in the Table 2.

Example 7

A testing device of Example 7 was manufactured in a similar manner to that of Example 1 except for that 0.05 mass % rather than 0.5 mass % of a polyvinylpyrrolidone aqueous solution was used, and stability of the compressional state, restorability, water releasing property, and leakage were evaluated. Results of the evaluation are shown in the Table 2.

Example 8

A testing device of Example 8 was manufactured in a similar manner to that of Example 1 except for that a AC sponge V (manufactured by A.C. Chemical, Inc.) processed to have the thickness of 1000 μm was used instead of Bell-eater D, and stability of the compressional state, restorability, water releasing property, and leakage were evaluated. Results of the evaluation are shown in the Table 2.

Example 9

A testing device of Example 9 was manufactured in a similar manner to that of Example 1 except for that a AC sponge U (manufactured by A.C. Chemical, Inc.) processed to have the thickness of 1000 μm was used instead of Bell-eater D, and stability of the compressional state, restorability, water releasing property, and leakage were evaluated. Results of the evaluation are shown in the Table 2.

Example 10

A testing device of Example 10 was manufactured in a similar manner to that of Example 1 except for that Bellclean E-1 (manufactured by AION co., Ltd) was used instead of Bell-eater D, and stability of the compressional state, restorability, water releasing property, and leakage were evaluated. Results of the evaluation are shown in the Table 2.

Example 11

A testing device of Example 11 was manufactured in a similar manner to that of Example 1 except for that Bell-eater FB was used instead of Bell-eater D, and stability of the compressional state, restorability, water releasing property, and leakage were evaluated. Results of the evaluation are shown in the Table 2.

Example 12

A testing device of Example 12 was manufactured in a similar manner to that of Example 1 except for that Bell-eater GB was used instead of Bell-eater D, and stability of the compressional state, restorability, water releasing property, and leakage were evaluated. Results of the evaluation are shown in the Table 2.

Example 13

A testing device of Example 13 was manufactured in a similar manner to that of Example 1 except for that a PVA sponge compressed without using a water soluble resin was used, and stability of the compressional state, restorability, water releasing property, and leakage were evaluated. As for the stability of the compressional state, the storage member of Example 13 did not include a water soluble resin for holding the compressed state of the sponge and, therefore, the stability was getting worse with the passage of time. Results of the evaluation are shown in the Table 2.

Example 14

A testing device of Example 14 was manufactured in a similar manner to that of Example 1 except for that the storage portion was formed by heat transfer, and stability of the compressional state, restorability, water releasing property, and leakage were evaluated.

<<Formation of a Storage Portion>>
<Manufacturing of a Transfer Member>
(1) Manufacturing of a Storage Member Forming Film A PVA sponge (Bell-eater D, manufactured by Fuji Chemical Industries, Ltd.) processed to have the thickness of 0.5 mm was sufficiently dipped in 0.5 mass % of a polyvinylpyrrolidone aqueous solution (Polyvinylpyrrolidone K15, manufactured by Tokyo Chemical Industry Co., Ltd.), an excessive solution was lightly removed from the dipped PVA sponge, and then the PVA sponge was compressed with a press machine (High Pressure Jack J-1, manufactured by Hayashi Kougyou Kabushikikaisha) at 28 MPa for 5 hours. The compressed PVA sponge was dried with a vacuum dryer at room temperature for 1 hour, thereby a storage material having thickness of 89 μm was obtained.

(2) Preparation for Application Liquid of a Separation Layer 14 pts by mass of polyethylene wax (manufactured by TOYO ADL CORPORATION, polywax 1000, melting point: 99° C., penetration at 25° C.: 2), 6 pts by mass of an ethylene-vinyl acetate copolymer (manufactured by DUPONT-MITSUI POLYCHEMICALS CO., LTD, EV-150, weight-average molecular weight: 2,100, VAc: 21%), 60 pts by mass of toluene, and 20 pts by mass of methyl ethyl ketone were mixed and dispersed so that 2.5 μm of the average particle diameter was obtained, thereby application liquid of a separation layer was obtained.

(3) Preparation for Application Liquid of Back Layer 16.8 pts by mass of emulsion of silicone rubber (manufactured by Shin-Etsu Chemical Co., Ltd., KS779H, solid content 30 mass %), 0.2 pts. by mass of a chloroplatinic acid catalyst, and 83 pts by mass of toluene were mixed, and then application liquid of a back layer was obtained.

(4) Formation of Each Layer

The application liquid of a back layer was applied onto one surface of a PET film (manufactured by Toray Industries, Inc., Lumirror F65), which was used as support 101, having the average thickness of 25 μm, and was dried at 80° C. for 10 minutes so that back layer 104 having the average thickness of 0.02 μm was formed. The application liquid of a separation layer was applied onto the other surface of the PET film than the surface over which the back layer was formed, and was dried at 40° C. for 10 seconds so that separation layer 102 having the average thickness of 20 μm was formed. The storage member where an indentation of a grid of 1 mm square was formed was laid over separation layer 102 and was compressed with a press machine at 28 MPa for 1 hour so that storage member forming layer 103 having the average thickness of 72 μm was formed, thereby a transfer member for forming the storage member was obtained as transfer member 100.

The transfer member for forming the storage member and a hydrophilic porous substrate having a hydrophobic substrate were overlaid, and thermal transfer was conducted under the following condition with a thermal transfer printer so that a storage portion having a width of 3.5 mm and a length of 45 mm was formed. The hydrophilic porous substrate having a hydrophobic substrate was the same as that used in Example 1. The storage portion was formed by using a thermal head having the head density of 300 dpi (manufactured by TDK Corporation) under the condition where the printing speed was 16.9 mm/sec and printing energy was 0.81 mJ/dot.

Comparative Example 1

<<Manufacturing of Assay Member>>
<Formation of a Testing Portion>
<Formation of a Test Line and a Control Line>

6 μL of an anti-human IgG antibody (4.7 mg/mL, I1886, manufactured by Sigma-Aldrich Corporation) was applied on a nitrocellulose membrane filter (HF180, manufactured by Merck Millipore) which was cut into a piece having a shape having a width of 3.5 mm and a length of 39 mm so that test line 12b having a width of 1 mm was formed. In a similar manner, 6 μL of human IgG (4.8 mg/mL, I2511-10MG, manufactured by Sigma Corporation) was applied on the nitrocellulose membrane filter so that control line 12c having a width of 1 mm was formed. After these processes, 16 hours of drying was conducted at room temperature, thereby a testing portion was formed.

<Manufacturing of a Marker Antibody Holding Pad>

Colloidal gold anti-human IgG (Gold 40 nm, OD=15, manufactured by BAW) was applied over a glass fiber pad (manufactured by Merck Millipore, CFCP203000) which was cut into a piece having a shape having a width of 3.5 mm and a length of 16 mm to be included at 60 μL/cm$^2$, and then it was dried under the reduced pressure over night so that a marker antibody holding pad was obtained.

<Assembly>

A nitrocellulose membrane filter (a paper substrate) where a testing portion was formed was adhered onto a PET film (manufactured by Toray Industries, Inc., Lumirror S10, 100 μm) at the portion having a distance of 32 mm from one end of the long side so that the PET film and the other surface of the surface where the testing portion was formed were faced each other. Then, a marker antibody holding pad was cut into a piece having a shape of a width of 3.5 mm and a length of 16 mm and was adhered onto the paper substrate so that the marker antibody holding pad overlapped with 2 mm of the upstream end of the paper substrate. Further, a sample pad (manufactured by Merck Millipore, Sure Wick C048) having a width of 3.5 mm and a length of 34 mm was placed on the upper surface of the marker antibody holding pad so as to have 16 mm of the overlapping portion, and adhered, thereby a sample dropping pad was obtained.

<Housing>

Figure 7A:
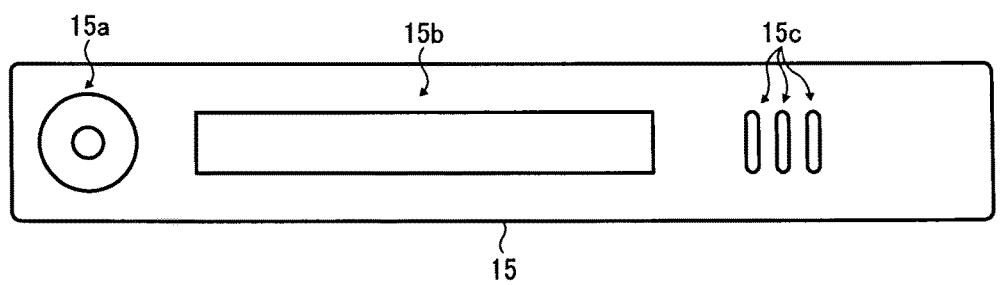
FIG. 7A, 7B are a case of a comparative example. A cross sectional view of the case including the test strip is shown in FIG. 7(B).
Figure 7B:
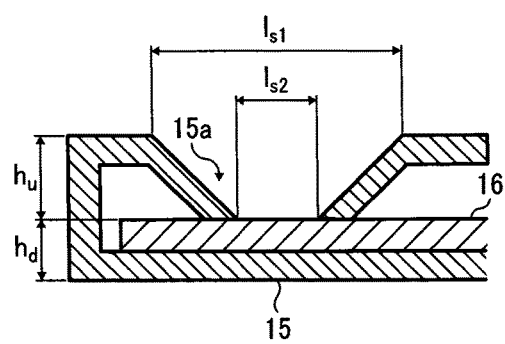

A top view of a case of Comparative Example 1 is shown in FIG. 7(A). A cross sectional view of the case including the test strip is shown in FIG. 7(B). In FIG. 7, $I_{s1}$ is 10 mm, $I_{s2}$ is 3 mm, $h_u$ is 3 mm, and $h_d$ is 5 mm. Plastic case 15 of FIG. 7 has a first opening 15a as the entry of a liquid test sample, a second opening 15b for sighting a test line and a control line, and a third opening 15c for a gas vent. A testing device for Immunochromatographic Assay was obtained by putting the test strip into case 15. In the testing device, a storage portion having a thickness of 3.48 mm was formed of the entry having 3 mm of $h_u$ and a sample pad having a thickness of 0.48 mm.

The Comparative Example was evaluated in the same manner as in Example 1. Results of the evaluation are shown in the Table 2.

Comparative Example 2

A testing device of Comparative Example 2 was manufactured in a similar manner to that of Comparative Example 1 except for that the test strip was not put into the housing case, and the water releasing property was evaluated. A plastic case as a tank temporary holding water was not provided, therefore water dropped onto the sample pad leaked from the testing device and did not spread out to the membrane.

Comparative Example 3

A testing device of Comparative Example 3 was manufactured in a similar manner as in Example 1 except for that the sponge was not compressed, and a water releasing property and leakage were evaluated.

Comparative Example 4

A testing device of Comparative Example 4 was manufactured in a similar manner to that of Example 1 except for that a urethane sponge (Everlight SF QP-16, manufactured by Brigestone) was used instead of a PVA sponge, and stability of the compressional state, restorability, water releasing property, and leakage were evaluated. Results of the evaluation are shown in the Table 2. In the evaluation of restorability, the dropped water was not held due to the hydrophobicity of the storage member, therefore the storage member was not restored.

Comparative Example 5

A testing device of Comparative Example 5 was manufactured in a similar manner to that of Example 1 except for that wax (Nissan Elector WEP-3, manufactured by NOF CORPORATION) was used instead of polyvinylpyrrolidone, and stability of the compressional state, restorability, water releasing property, and leakage were evaluated. Results of the evaluation are shown in the Table 2. In the evaluation of restorability, the dropped water was not held due to the water insolubility of the wax, therefore the storage member was not restored.

TABLE 1

| | A storage member | | | Water soluble resin Tyeps of resin |
|---|---|---|---|---|
| | Porous synthetic resin or a sample dropping pad | Porosity (%) | Average pore diameter (μm) | |
| Example 1 | Bell-eater D | 89 | 80 | PVP |
| Example 2 | Bell-eater D | 89 | 80 | PEO |
| Example 3 | Bell-eater D | 89 | 80 | PVA |
| Example 4 | Sofras | 83 | 25 | PVP |
| Example 5 | Bell-eater D | 89 | 80 | PVP |
| Example 6 | Bell-eater D | 89 | 80 | PVP |
| Example 7 | Bell-eater D | 89 | 80 | PVP |
| Example 8 | AC sponge V | 75 | 60 | PVP |
| Example 9 | AC sponge U | 75 | 15 | PVP |
| Example 10 | Bell-clean E-1 | 90 | 130 | PVP |
| Example 11 | Bell-eater FB | 91 | 300 | PVP |
| Example 12 | Bell-eater GB | 90 | 700 | PVP |
| Example 13 | Bell-eater D | 89 | 80 | None |
| Example 14 | Bell-eater D | 89 | 80 | PVP |
| Comp. Ex. 1 | Sure Wick C048 | | | |
| Comp. Ex. 2 | Sure Wick C048 | | | |
| Comp. Ex. 3 | Bell-eater D | 89 | 80 | None |
| Comp. Ex. 4 | Everlight SF QP-16 | 97 | 1400 | PVP |
| Comp. Ex. 5 | Bell-eater D | 89 | 80 | Wax |

TABLE 2

| | A storage member Thickness | Evaluation | | | | |
|---|---|---|---|---|---|---|
| | | Case | Leakage | Stability | Water releasing property | Restorability |
| Example 1 | 169 | not in use | ○ | 1.02 | 76 | 100 |
| Example 2 | 148 | not in use | ○ | 1.03 | 74 | 100 |
| Example 3 | 157 | not in use | ○ | 1.02 | 75 | 100 |
| Example 4 | 88 | not in use | ○ | 1.04 | 70 | 100 |
| Example 5 | 162 | not in use | ○ | 1.05 | 75 | 100 |
| Example 6 | 171 | not in use | ○ | 1.02 | 76 | 100 |
| Example 7 | 144 | not in use | ○ | 1.06 | 74 | 100 |
| Example 8 | 176 | not in use | X | 1.03 | 73 | 100 |
| Example 9 | 182 | not in use | X | 1.05 | 74 | 100 |
| Example 10 | 142 | not in use | ○ | 1.02 | 75 | 100 |
| Example 11 | 243 | not in use | ○ | 1.03 | 74 | 100 |
| Example 12 | 1538 | not in use | X | 1.05 | 88 | 100 |
| Example 13 | 171 | not in use | ○ | 1.18 | 75 | 100 |
| Example 14 | 89 | not in use | ○ | 1.02 | 76 | 100 |
| Comp. Ex. 1 | 3480 | in use | X | | 76 | |
| Comp. Ex. 2 | 480 | not in use | X | | | |
| Comp. Ex. 3 | 1000 | not in use | ○ | | 74 | |
| Comp. Ex. 4 | 171 | not in use | X | 1.03 | unevaluable | 0(unevaluable) |
| Comp. Ex. 5 | 171 | not in use | X | 1.02 | unevaluable | 0(unevaluable) |

The invention claimed is:

1. A testing device comprising:
a flow path member for a liquid test sample,
a storage member that stores the liquid test sample to be supplied to the flow path member and is in contact with a portion of a flow path of the flow path member, and
a testing material for testing the liquid test sample supplied to the flow path,
wherein the storage member is expandable upon contacting with the liquid test sample, and
wherein the storage member comprises a porous synthetic resin and a water soluble resin.

2. The testing device according to claim 1, wherein the storage member is a shape elastic material.

3. The testing device according to claim 1, wherein the storage member forms an open-cell structural body by expansion.

4. The testing device according to claim 3, wherein a porosity of the open-cell structural body is 80% or more.

5. The testing device according to claim 3, wherein an average pore diameter of the open-cell structural body is from 20 μm to 300 μm.

6. The testing device according to claim 1, wherein the water soluble resin has thermoplasticity.

7. A transfer member comprising:
a support,
a release layer, comprising a wax and a binder resin, over the support, and
a storage member forming layer overlapping with the release layer and comprising a storage member by expansion brought from a contact with a liquid test sample,
wherein the support, the release member, and the storage member are laminated to form a multilayer structure, and wherein the storage member comprises a porous synthetic resin and a water soluble resin.

8. A manufacturing method of a testing device, the method comprising: providing the transfer member of claim 7, and
transferring the storage member forming layer of the transfer member of claim 7 to a portion of a flow path member by compressing the storage member forming layer and the flow path member when the storage member forming layer and the flow path member face each other.

9. A testing kit comprising the testing device of claim 1 and a sampler for sampling a liquid test sample.

10. The testing device according to claim 1, further comprising a substrate on which the flow path member is formed.

11. The testing device according to claim 1, further comprising an absorbent member in contact with a portion of the flow path member.

12. The testing device according to claim 1, wherein the water soluble resin is at least one selected from the group consisting of polyvinylpyrrolidone (PVP), polyvinyl alcohol (PVA), polyethylene glycol (PEG), and polyethylene oxide (PEO).

13. The testing device according to claim 1, wherein the flow path member comprises a hydrophilic porous material.

14. The testing device according to claim 13, wherein the hydrophilic porous material has an open-cell structural body wherein pores are connected with each other.

15. The testing device according to claim 14, wherein a porosity of the hydrophilic porous material is from 40% to 90%.

16. The testing device according to claim 1, wherein a content of the water soluble resin in the storage member is from 0.05 mass % to 0.6 mass % of the total mass of the storage member.

17. The testing device according to claim 1, further comprising a conjugation part, a test line, and a control line on the flow path member.

18. The transfer member of claim 7, wherein the storage layer is formed on the top of the release layer.

19. The transfer member of claim 18, further comprising a back layer, wherein the support is formed on the top of the back layer.

* * * * *

UNITED STATES PATENT AND TRADEMARK OFFICE
CERTIFICATE OF CORRECTION

PATENT NO. : 10,184,938 B2
APPLICATION NO. : 15/065955
DATED : January 22, 2019
INVENTOR(S) : Rie Kobayashi It is certified that error appears in the above-identified patent and that said Letters Patent is hereby corrected as shown below:

On the Title Page

Item (73), the Assignee's information is incorrect. Item (73) should read:
--(73) Assignee: Ricoh Company, Ltd., Tokyo (JP)--

Signed and Sealed this
Seventeenth Day of September, 2019

Andrei Iancu
*Director of the United States Patent and Trademark Office*